United States Patent
Shi et al.

(10) Patent No.: US 10,233,439 B2
(45) Date of Patent: Mar. 19, 2019

(54) DIRECTED MODIFICATION OF GLUCOSAMINE SYNTHASE MUTANT AND APPLICATION THEREOF

(71) Applicants: Yangzhou Rixing Bio-Tech Co.,Ltd, Gaoyou (CN); Jiangnan University, Wuxi (CN)

(72) Inventors: Jinsong Shi, Wuxi (CN); Zhenghong Xu, Wuxi (CN); Chao Zhang, Gaoyou (CN); Jinsong Gong, Wuxi (CN); Heng Li, Wuxi (CN); Zhenzhong Ding, Gaoyou (CN); Xiang Fang, Gaoyou (CN); Wanhong Zhang, Gaoyou (JP)

(73) Assignees: Yangzhou Rixing Bio-Tech Co., Ltd, Gaoyou (CN); Jiangnan University, Wuxi (CN)

( * ) Notice: Subject to any disclaimer, the term of this patent is extended or adjusted under 35 U.S.C. 154(b) by 38 days.

(21) Appl. No.: 15/613,286

(22) Filed: Jun. 5, 2017

(65) Prior Publication Data

US 2018/0312829 A1 Nov. 1, 2018

(30) Foreign Application Priority Data

Apr. 26, 2017 (CN) .......................... 2017 1 0282955

(51) Int. Cl.
| | |
|---|---|
| *C12N 9/10* | (2006.01) |
| *C12P 19/02* | (2006.01) |
| *C12P 13/00* | (2006.01) |
| *C12N 15/09* | (2006.01) |
| *C12N 15/70* | (2006.01) |
| *C12P 19/26* | (2006.01) |

(Continued)

(52) U.S. Cl.
CPC ............... *C12N 15/09* (2013.01); *C12N 9/10* (2013.01); *C12N 9/1096* (2013.01); *C12N 15/70* (2013.01); *C12P 19/02* (2013.01); *C12P 19/26* (2013.01); *C12Y 206/01016* (2013.01); *C07H 5/06* (2013.01); *C07H 11/04* (2013.01); *C12N 9/00* (2013.01)

(58) Field of Classification Search
None
See application file for complete search history.

(56) References Cited

U.S. PATENT DOCUMENTS 7,332,304 B2 * 2/2008 Deng ..................... C12N 15/52
435/15

* cited by examiner

*Primary Examiner* — Yong D Pak
(74) *Attorney, Agent, or Firm* — Gokalp Bayramoglu

(57) ABSTRACT

The present invention discloses a directionally modified glucosamine synthase mutant and its application. The amino acid sequence of the glucosamine synthase mutant is as shown in sequence list SEQ ID No. 1, and the nucleotide sequence is as shown in sequence list SEQ ID No. 2. The genetic engineering bacteria of glucosamine synthase is successfully constructed. In order to improve the tolerance of recombinant bacteria against glucosamine, the glucosamine synthase is directionally modified. A glucosamine synthase mutant is selected from the mutant library via high-throughput screening method, the amino acid changes in the mutant induces the spatial conformational change in the enzyme, so as enlarged the region where the enzyme and substrate combines, therefor the combination efficiency of the enzyme and the substrate is increased. The glucosamine synthase of the present invention has various advantages, such as rich in raw material of glucose, and a convenient subsequent extraction.

3 Claims, 4 Drawing Sheets

Specification includes a Sequence Listing.

(A)

(B)

(51) Int. Cl.
*C12N 9/00* (2006.01)
*C07H 11/04* (2006.01)
*C07H 5/06* (2006.01)

(A) (B)

DIRECTED MODIFICATION OF GLUCOSAMINE SYNTHASE MUTANT AND APPLICATION THEREOF

CROSS REFERENCE TO RELATED APPLICATIONS

This application is based upon and claims priority to Chinese Patent Application No. 201710282955.4 (CN), filed on Apr. 26, 2017, the entire contents of which are incorporated herein by reference.

TECHNICAL FIELD

The present invention relates to the field of biotechnology, specifically relating to a directionally modified glucosamine synthase mutant and its application.

BACKGROUND

Glucosamine, GlcN in short, the main component of proteoglycans and glycoproteins, exists in various organisms and can be translated into glucose-6-phosphate inside the cell through amination. N-acetyl-d-glucosamine (GlcNAc) is widely used in medicine, food, daily chemical and other fields. Traditionally, the GlcNAc is produced by acid hydrolysis, using the chitin of shrimps and crabs as raw material. The reaction requires concentrated acid and high temperature conditions, which will cause serious environmental pollution, and the equipment requirement is strict and the production cost is high. With the rapid development of metabolic engineering and synthetic biology, biological fermentation method used in the industrial yield is becoming more and more mature. The glucose is used as a raw material to directly convert into glucosamine, which has the advantages of low material cost, simple extraction, high purity of the product, less pollution and so on.

Glucosamine synthase (GLS) is the key enzyme of GlcN biosynthesis, which can catalyze fructose-6-phosphate to generate GlcN-6-P with the glutamine as amino donor. This is the first rate-limiting reaction in the synthesis pathway of GlcN, and GLS is seriously affected by the product inhibition effect of the metabolite GlcN-6-P. Therefore, GlcN-6-P cannot be largely accumulated in the normal metabolic synthesis. In order to reduce the inhibition of the product, co-expression of glucosamine acetyltransferase gene is usually used in the E. coli system to convert the GlcN-6-P in the metabolic system into GlcNAc-6-P with a small stimulation Both the product GlcN-6-P and GlcNAc-6-P can be transferred from intracellular to extracellular, and be dephosphorylated into GlcNa and GlcNAc respectively, while GlcNAc can be converted into GlcN through deacetylation under the acidic condition. The low biosynthetic ability and poor tolerance to the product of GLS are the main reasons that limit the increase in the yield. Although strains used in current industrial yield have far exceeded the level, most of which were optimized through metabolic engineering and fermentation control, but the literature analysis shows that one focus of the transformation is glucosamine synthase.

SUMMARY OF THE INVENTION

The present invention is intended to provide a method for constructing engineering bacteria with high yield of glucosamine through cloning and expressing of glucosamine synthase via gene engineering and modification of glucosamine synthase via error-prone PCR. This method is a simple and effective technique for obtaining DNA sequence variation of specific genes, which has great application prospect in genetic research and genetic improvement studies. The method has the advantages of short cycle, low energy consumption and less pollution, and it's suitable for the requirements of industrial yield.

To provide a new transformation strategy to modify the GLS, better expression plasmid and expression hosts are firstly screened, and then the error-prone PCR is used to irrationally modify the GLS. Glucosamine is added into the medium as screening pressure to screen the mutant strains with enhanced tolerance. In addition, the invention also attenuates the inhibitory effect of GlcN accumulation to the host cell through co-expressing the glucosamine acetyltransferase GNAL, and to investigate the synthesis ability of mutation strains.

A directionally modified glucosamine synthase mutant, consisting of the amino acid sequence shown in sequence list SEQ ID No. 1.

The gene of the directionally modified glucosamine synthase mutant, consisting of the nucleotide sequence shown in sequence list SEQ ID No. 2.

A genetic engineering bacteria carrying a gene of the directionally modified glucosamine synthase mutant are included.

An application of the directionally modified glucosamine synthase mutant in the biosynthesis of glucosamine, through a co-expression of glucosamine acetyltransferase, glucosamine of the fermentation system is converted into acetylated glucosamine to reduce the product inhibitory effect and improve yield of glucosamine.

A method for directional modifying glucosamine synthase via genetic engineering method comprises cloning and expressing the glucosamine synthase gene, establishing a mutant library using the continuous error-prone PCR for high-throughput screening to obtain glucosamine synthase mutant M15-9 with improved fermentation performance.

The amino acid sequence of the modified glucosamine synthase comparing with the wild-type, the Ala residue at position 60 is changed into Ser, Val at position 128 is changed into Ala, Asp at position 352 is changed into Ala, Arg at position 354 is changed into Cys, Iie at position 422 is changed into Met, Leu at position 423 is changed into Val, Asp at position 471 is changed into Glu, Leu at position 567 is changed into Glu. The mutation is a cumulative result of several rounds. Structure analysis showed that the hydrophobicity of the mutant enzyme increased significantly compared to the wild-type, resulting in the gathering of the residues in the active center inwards or sideways. At the same time, the hydrogen bond of the mutant enzyme is strengthened. Besides, the negatively charged amino acids are significantly reduced and converted into neutral amino acids, which weakens the polarity of the enzyme and benefits the combination of enzyme and substrate. The above changes change the spatial conformation of the enzyme, increase the combination region of enzyme and substrate, and improve the combination efficiency of enzyme and substrate.

Compared to prior art, the present invention has the following benefits: The present invention clones and expresses glucosamine synthase through gene engineering. The best expression system is optimized through the screening of different expression plasmids and hosts. Given E. coli as an example, the engineering bacteria of E. coli Rosettagami (DE3)-pET-24a-gls is successfully constructed and obtained, and its detected glucosamine yield of glucosamine is 1.63 g/L. In order to improve the tolerance of the recombinant bacteria against glucosamine, the glucosamine is directionally modified by error-prone PCR technology. A high productive GlcN bacterial strain is screened from about 2700 mutant strains via high throughput screening method. The GlcN yield reaches 3.57 g/L, which is 1.19 times as compared to that of starting strain. As the accumulation of GlcN inhibits the growth and metabolism of the glucosamine synthase recombinant bacteria, it is further converted into acetylated glucosamine GlcNAc through co-expression of glucosamine acetyltransferase GNAL in the present invention to reduce the inhibitory effect of the product. The result shows that the tandem expression of GNAL and GLS can significantly improve the fermentation ability of the bacteria strains, and the cumulative yield of GlcN and GlcNAc reaches 7.83 g/L, which is 2.19 times as compared to that of the single expression of GLS. After a test of the preliminary flask fermentation optimization and 5 L tank fermentation, the results show that the glucosamine fermentation level is basically stable, the highest yield after 22 hours' fermentation reaches 9.85 g/L.

DETAILED DESCRIPTION OF THE EMBODIMENTS

The embodiments of the present invention are described in detail below. The scope of the present invention is not limited by the specific embodiments.

Embodiment 1

Design primers according to the gls gene, the primer in 5' terminal is gls (1), the primer in 3' terminal is gls (2). Design primers according to the gnal gene the primer in 5' terminal is gnal (1), the primer in 3' terminal is gnal (2). The primer sequences related in the present invention are shown in table 1.

TABLE 1

The primers used in the experiment.

| Name | Primer sequence (5'-3') | Retriction sites |
|---|---|---|
| gls(1) | CGCGGATCCATGTGTGGAATCGTAGGTTAT | BamH I |
| gls(2) | CCGGAATTCTTATTCAACGGTCACGCTTTTGGC | EcoR I |
| gnal(1) | CCCAAGCTTAAGGAGATATACCATGAGCCTGCCGGATGGTTTT | Hind III |
| gnal(2) | CCGCTCGAGTTATTTACGAATTTGCATTTCGAC | Xho I |

Figure 1:
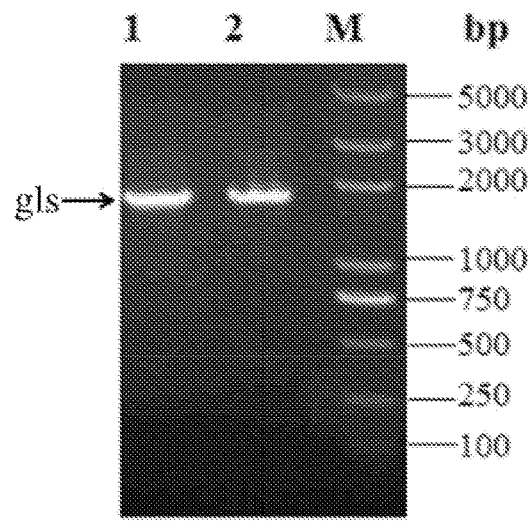
FIG. 1 is a gene amplification electrophoretogram of gls.
In the figure, M: Marker: lane 1 and lane 2: gls gene obtained from PCR, the target band can be seen in about 1800 bp.

The gls gene is cloned by primers gls (1) and gls (2). Extaq polymerase is used to amplify in the reaction. The reactions are carried out in a 50 µL reaction system with the following PCR conditions: pre-denaturation at 94° C. for 10 min; denaturation at 94° C. for 30 s, annealing at 62° C. for 45 s, extending at 72° C. for 60 s, 35 cycles; final extending at 72° C. for 10 min. The PCR product is electrophoresed on 1.0% agarose gel (FIG. 1) and the target sequences are collected. The g/s is ligated to pMD19-T to construct cloning plasmid, and the cloning plasmid and expression plasmid are digested respectively by BamH I and EcoR I, then expression plasmid is reconstructed through $T_4$ ligase reaction.

Embodiment 2

Figure 2:
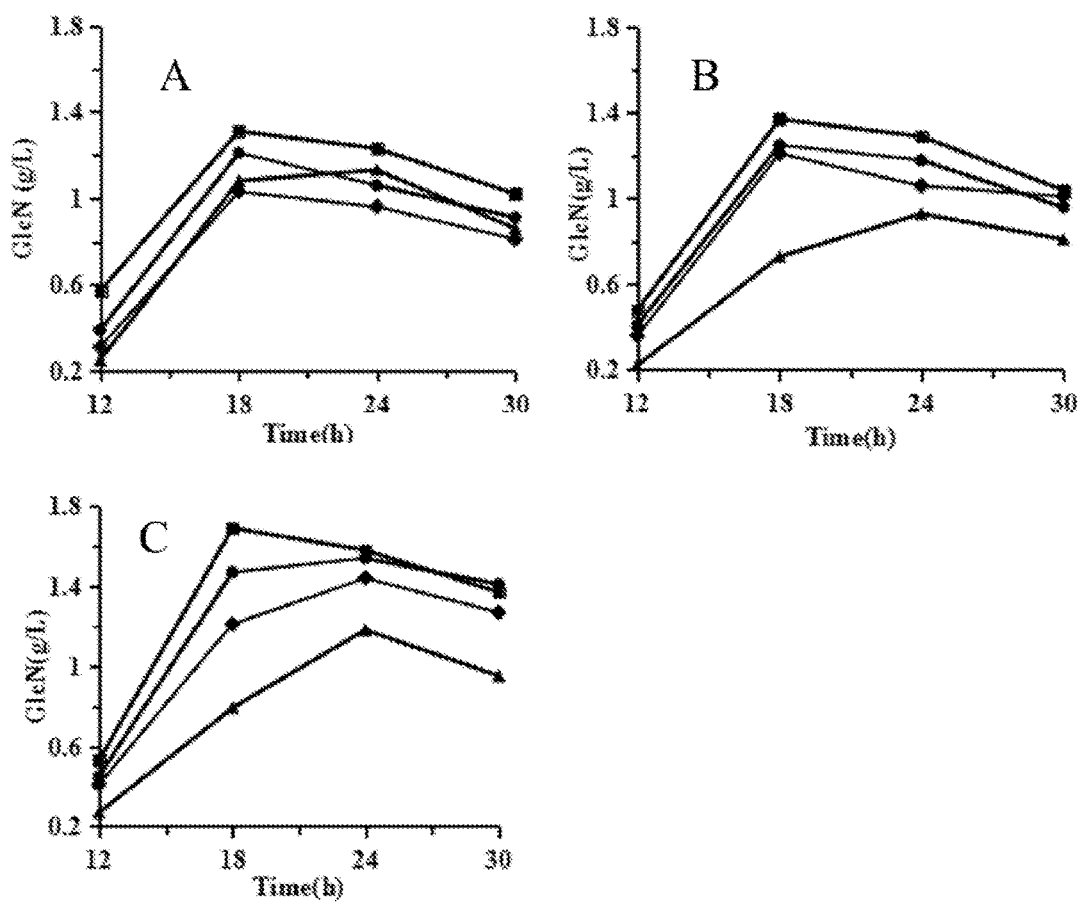
FIG. 2 is an optimization graph of the expression plasmids and expression hosts.
In the figure, •: pET-28a, ■: pET-24a, ▲: pRSFDuet-1, ♦: pET-22b, A: the expression host of *E. coli* BL21(DE3); B: *E. coli* BL21(DE3) plss; C: *E. coli* Rosetta-gami(DE3).

Four different expression plasmid, pET-22b, pET-24a, pET-28a and pRSFduet-1 are selected respectively. The expression plasmids are conducted enzyme digestion by EcoR I and BamH I. Gls is connected to the expression plasmids through the $T_4$ ligase to construct the recombinant plasmids pET-22b-gls, pET-24a-gls, pET-28a-gls and pRSFduet-1-gls respectively. *E. coli* Rosetta-gami (DE3), *E. coli* BL21 (DE3), *E. coli* BL21 (DE3) plss are taken as expression host to establish different gls recombinant expression systems. IPTG is added into the positive clone after screening to conduct induced expression. The result shows that when pET-24a is taken as expression plasmid, the expression system obtained the highest glucosamine synthesis ability, which reaches at 1.31 g/L, 1.37 g/L and 1.63 g/L in *E. coli* BL21 (DE3), *E. coli* BL21 (DE3) plss and *E. coli* Rosetta-gami (DE3) respectively (See FIG. 2).

Embodiment 3

In order to improve the tolerance of glucosamine synthase against glucosamine and the yield ability of glucosamine, the glucosamine synthase is conducted to directional modify the GLS via error-prone PCR. The reaction system of error-prone PCR after optimization is as shown in table 2:

TABLE 2

The reaction system of error-prone PCR

| Reagent | volume (μL) |
|---|---|
| error-prone PCR Mix, 10x | 3 |
| Special dNTP for error-prone PCR, 10x | 3 |
| MnCl$_2$, 5 mM | 4 |
| DNA template | 1 |
| Special GTP for error-prone PCR | 1 |
| gls(1) | 1 |
| gls(2) | 1 |
| Taq DNA polymerase | 1 |
| ddH$_2$O | 15 |
| Total | 30 |

The PCR reaction condition: starts with pre-denaturation at 94° C. for 10 min; followed by 30 cycles of denaturation at 94° C. for 30 s, annealing at 62° C. for 45 s, extending at 72° C. for 60 s; with a final extending at 72° C. for 10 min. After PCR reaction, PCR products are conducted 1.0% agarose gel electrophoresis. The target bands are excised from the gel and eluted using Elution buffer to conduct re-dissolution. The PCR product is conducted 1.0% agarose gel electrophoresis to gel extract the target sequences through the gel extraction kit. The gls and pET-24a are conducted double enzyme digestion by BamH I and EcoR I, then pET-24a-gls recombinant plasmid is constructed through T$_4$ ligase reaction.

Embodiment 4

The mutant recombinant plasmid is converted into *E. coli* Rosetta-gami (DE3), transferring to be conducted domestication in 5 mL LB medium contained 25 g/L of glucosamine, culturing under the condition of 37° C., 220 rpm for 10 h. The cultured bacterial fluid is coated on the solid plate containing 25 g/L of glucosamine and cultured in the 37° C. incubator for 12 h, the growth situation of the bacterial colony is real-time monitored. The transformant is selected and transferred into the TB liquid medium containing 3% of glucose to culture in the 96-deep well cultural plate, at the same time, each of the selected bacterial strain is made superscript in the well cultural plate. Each well correspond to a positive transformant, while two wells are reserved as contrast, one added with the starting strain, the other added with the culture medium only but no any strains. The culture condition is 37'C, 220 rpm. When the OD$_{600}$ is 0.6-0.8 in culture, the IPTG with a final concentration of 0.5 mM is added into and conducted induction of enzyme yield, and the culture condition changes into 25° C., 220 rpm. The glucosamine content is determined after fermentation for 24 h.

After the fermentation, the deep well plate is taken out to conducted centrifugation, and then 100 μL acetylacetone reagent is added into the deep well plate. And then the deep well plate is fixed in a water bath at 90° C. to conduct water bath for 1 h. After removed out from the water bath and cooled down, 1 mL of 96% ethanol is added to the deep well plate, and then 100 μL DMAB reagent is added. Then coloring at room temperature for 1 h, after that, 200 μL of the sample is corresponding sucked from the deep well plate to the 96-deep well plate by a volley. The 96-well plate is placed on a microplate reader to measure the spectrophotometric values at 530 nm to screen out the strains whose OD$_{530}$ are higher than that of the starting strain. The screened strains are selected from the plate to culture and measure the yield of GlcN.

Figure 3:
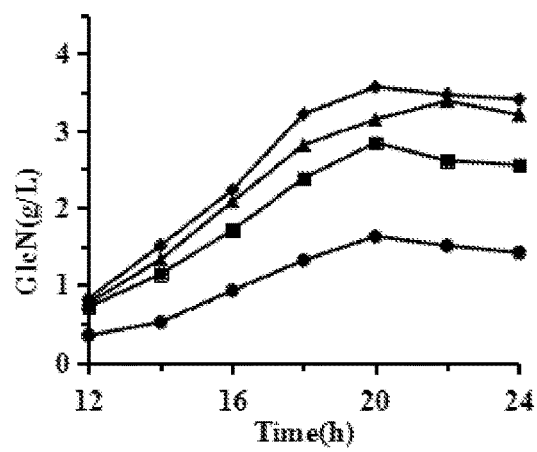
FIG. 3 is the GlcN yield of the mutant strain.
In the figure, •: Original strain; ■: The first round of optimal mutant; ▲: The second round of optimal mutant; ♦: The third round of optimal mutant.

The pET-24a-gls is taken as a template in the experiment. When gls is mutated in vitro via error-prone PCR technology, the high concentration GlcN is applied to conducted domestication to select the mutant strains through high throughput screening on the 96-well plate. 22 mutant strains with improved yield traits are screened from 1152 cloned strains in the first round of error-prone PCR. After screening verification, the yield of the mutant strain numbered M4-27 is 2.84 g/L, increased by 74.2%. Plasmids of the mutant strain are extracted as a template to conduct the next round of mutation and screening, 15 mutant strains are selected from 864 cloned strains. The highest yield is 3.39 g/L (Number M6-9). 20 mutant strains are selected from 691 cloned strains in the third round experiment, the highest yield reaches 3.57 g/L (Number M15-9), the yield of which cumulatively increased by 119% (See FIG. 3).

Embodiment 5

The original strain MO-0 and the best mutant strain M15-9 are inoculated in the LB seed culture medium, and transferred to ferment in the TB (3% glucose) fermentation medium under the condition of 37° C., 220 r/min. When OD$_{600}$ of bacterial fluid reaches 0.6-0.8, the IPTG is added into the fermentation broth and conducted induction at 25° C., the final concentration of IPTG is 0.5 mmol/L. The yield is determined after fermentation is conducted for 18 hs' later. The comparison of each indexes of wild bacteria and mutant bacteria is as shown in table 3.

TABLE 3

The fermentation indexes comparison of shake flask

| Fermentation parameters | Wild type | M4-27 | M6-9 | M15-9 |
|---|---|---|---|---|
| GlcN (g/L) | 1.48 ± 0.22 | 2.57 ± 0.17 | 3.32 ± 0.31 | 3.79 ± 0.54 |
| DCW (g/L) | 3.52 ± 0.14 | 3.22 ± 0.09 | 3.49 ± 0.17 | 3.15 ± 0.33 |
| Glucose consumption (g/L) | 22.27 ± 1.83 | 20.85 ± 1.52 | 23.03 ± 2.14 | 22.17 ± 2.92 |
| GlcN production intensity (gL$^{-1}$h$^{-1}$) | 0.08 ± 0.01 | 0.14 ± 0.01 | 0.18 ± 0.02 | 0.21 ± 0.03 |
| Conversion of glucose to GlcN (%) | 6.65 ± 0.99 | 12.33 ± 0.82 | 14.42 ± 1.35 | 17.10 ± 2.44 |
| Specific enzyme activity (%) | 100 | 161.43 ± 3.82 | 188.93 ± 5.37 | 197.17 ± 7.27 |

By controlling the content of MnCl$_2$ and dGTP in the reaction system in the embodiment, the base mutation rate is controlled within 2-3% to ensure the positive mutations can be obtained in each round of mutant strains. The mutational bases and amino acid sites of each round are shown in Table 4. The strain M15-9 with high and stable yield is obtained through multi-round advantage accumulation. The nucleotide sequence of the mature protein of the mutant enzyme is as shown in SEQ ID NO.2 and the amino acid sequence of which is as shown in SEQ ID NO. 1. The amino acid sequence of the wild-type glucosamine synthase is as shown in SEQ ID NO.3 and the amino acid sequence of which is shown as SEQ ID NO.4.

TABLE 4

Mutational bases and amino acid

| Strains | Base site | Mutant base | Amino acid site | Amino acid mutation |
|---|---|---|---|---|
| Wild type | — | — | — | — |
| First round M4-27 | 382 | T-C | 128 | V-A |
|  | 1054 | A-C | 352 | D-A |
|  | 1412 | T-G | 471 | D-E |
| Second round M6-9 | 1666 | T-C | 556 | L-P |
|  | 1293 | C-G | 432 | L-V |
|  | 1698 | T-A | 567 | V-E |
| Third round M15-9 | 177 | G-T | 60 | A-S |
|  | 1059 | C-T | 354 | R-C |
|  | 1265 | T-G | 422 | I-M |

Construction of glucosamine synthase model: The online software SWISS-MODEL is used to conduct homology modeling to obtain the three-dimensional structure model of glucosamine synthase via protein sequences analysis with high internal homology from the protein database (PDB). Through sequence and structure analysis show that there are two sites changed near the active center 5 Å of the three-dimensional structure in glucosamine synthase. The changes of mutation sites 352 (D-A) and 354 (R-C) have a significant influence to the combination region of the substrate fructose-6-phosphate. Specific changes are as follows:

① Comparison of Hydrophobic

Figure 4:
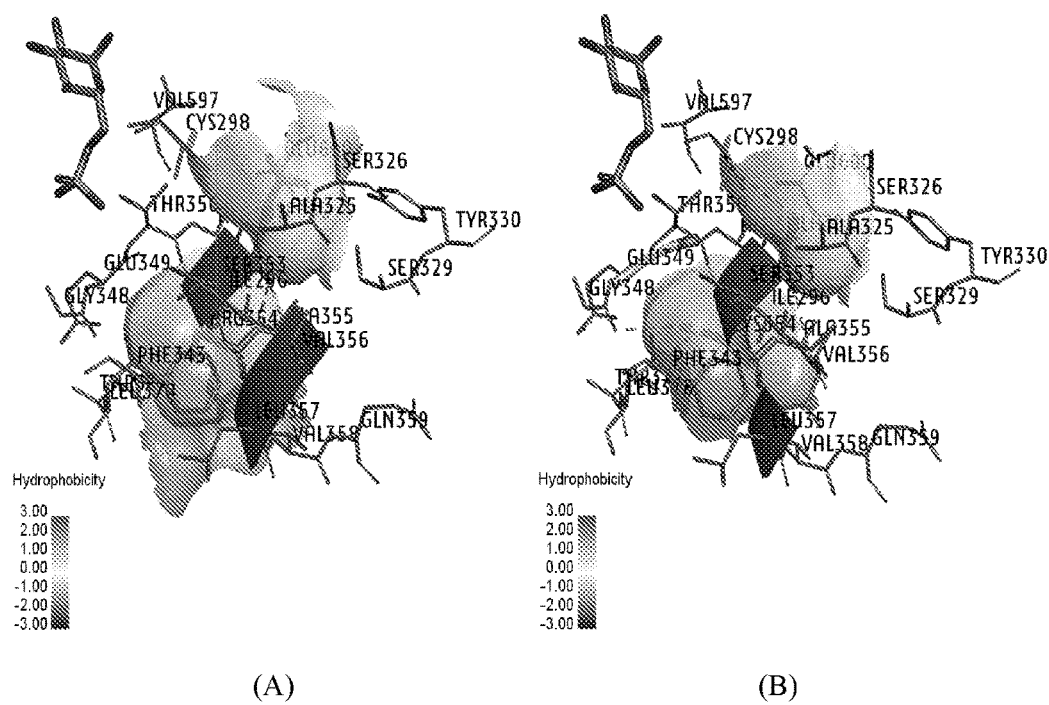
FIG. 4 is the comparison diagram of hydrophobicity of wild enzyme and mutant enzyme M15-9.
In the figure, (A) is wild-type enzyme, (B) is mutant enzyme M15-9.

As FIG. 4B shows, the changes in amino acid residues of the enzyme lead to the increasing of hydrophobic of the mutant enzyme compared to the wild type, which causes the residues of enzyme active center to gather insides or sideways that changes the spatial conformation of the enzyme. Further, the combination region of the enzyme and substrate is enlarged and the combination efficiency of the enzyme is improved.

② Comparison of Hydrogen Bonds

Figure 5:
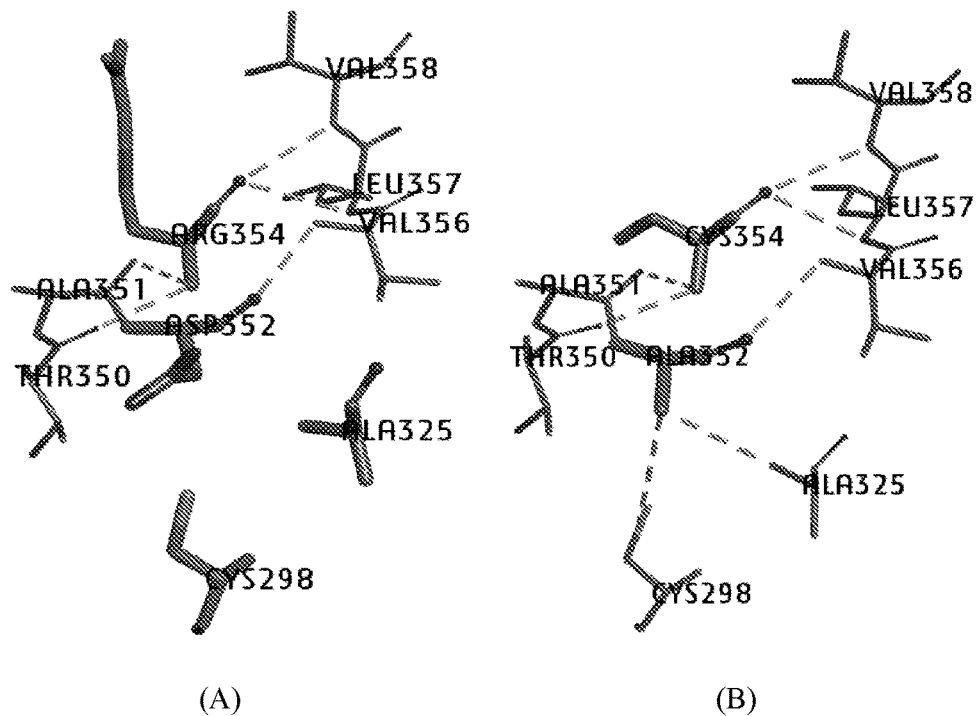
FIG. 5 is the comparison diagram of the hydrogen bonds of the two enzymes.
In the figure, (A) is wild-type enzyme, (B) is mutant enzyme.
Figure 6:
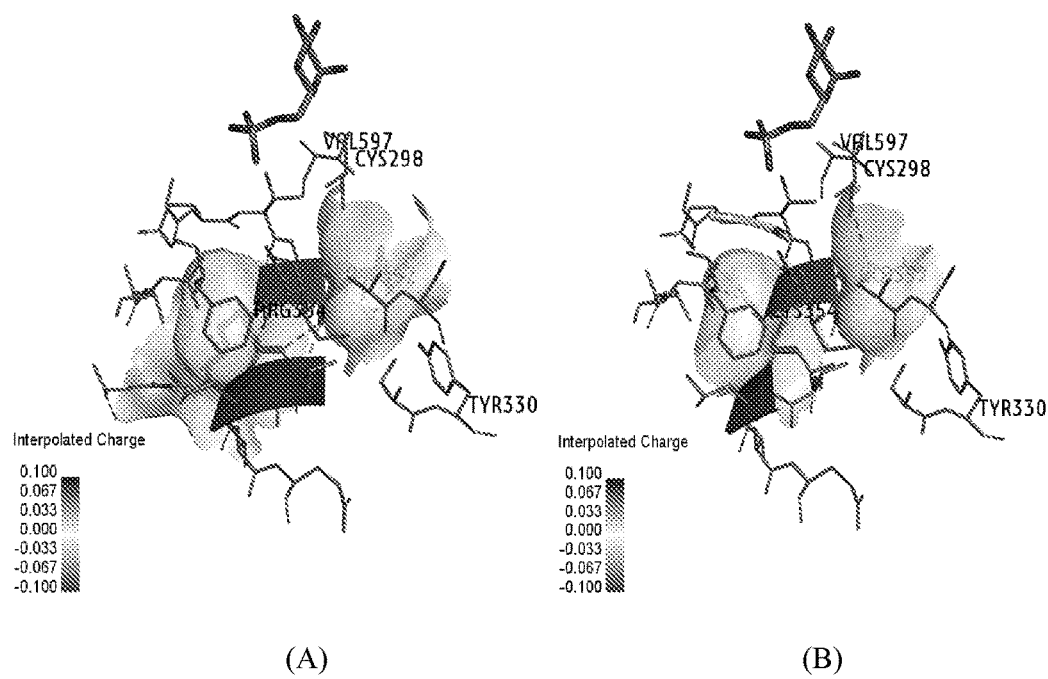
FIG. 6 is the comparison diagram of the electric charge of the two enzymes.
In the figure, (A) is wild-type enzyme, (B) is mutant enzyme.

As shown in FIG. 5 (A), the wild-type enzyme contains 5 hydrogen bonds, while there are 7 hydrogen bonds in the mutant one as shown in FIG. 5 (B), which enhanced the hydrogen bond in the active center. The hydrogen bonding and hydrophobic interaction play an important role in maintaining the stability of three-dimensional conformation of enzyme molecules. The hydrogen bonds are connected around the active center to enhance hydrophobic interactions between nonpolar groups, and make the three-dimensional conformation of the enzyme molecules more stable. The change of residues leads to the increase, decrease, and the interaction of hydrogen bonds, which affects the spatial structure of enzymes, so that the three-dimensional conformation of enzyme molecules is affected, and the combination efficiency of enzymes and substrates is improved.

③ Comparison of the Charge

The change in amino acid residues of the enzyme leads to the significant reduction of the negatively charged amino acids of the mutant enzyme compared to wild type as shown in FIG. 4B. The negatively charged amino acids changing into neutral amino acids weaken the polarity of the enzyme molecule, which is more beneficial to the combination region of enzymes and substrates, and the combination efficiency of the enzyme is improved.

Embodiment 6

Figure 7:
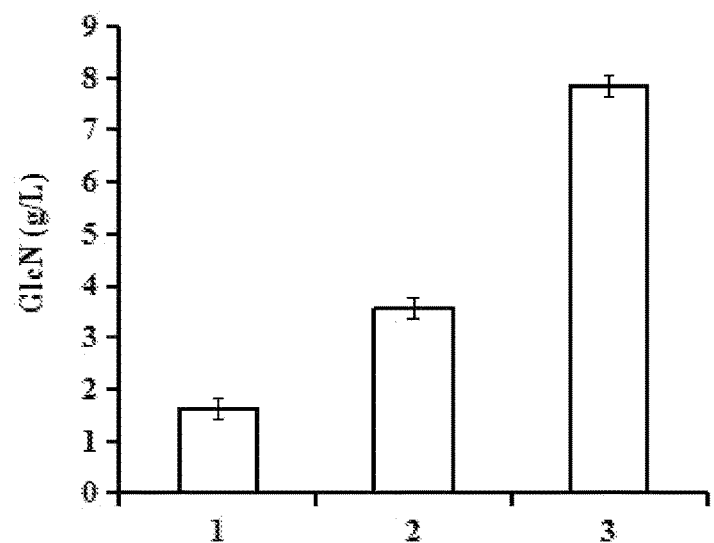
FIG. 7 is the GlcN yield of the co-expression recombinant bacteria.
In the figure, 1 referred to recombinant bacteria with no gls mutation; 2 referred to recombinant bacteria with a gls mutation; 3 referred to recombinant bacteria co-expresses both gls and gnal after the mutation.

Because of its less stimulation to cells and ability to conduct deacetylation to convert into GlcN by weak acid in the downstream extraction process, the acetylglucosamine is often chosen as the fermentation product. The gnal gene is amplified by primer gnal (1) and gnal (2). The PCR product is conducted 1.0% agarose gel electrophoresis to gel extract the target sequences, then the gls and pET-24a-gls are conducted double enzyme digestion by Hind III and Xho I, after then pET-24a-gls recombinant plasmid is constructed through $T_4$ ligase reaction. The recombinant plasmids are transformed into *E. coli* Rosetta-gami (DE3). The successfully validated positive clones are introduced into the fermentation medium. When the $OD_{600}$ of bacterial fluid reaches 0.6-0.8 in the fermentation under the condition of 37° C., 250 r/min, IPTG of a final concentration at 0.5 mmol/L is added into the fermentation broth, and transfer to conduct induction at 25° C. The content of GlcN and GlcNAc is determined after fermentation for 18 h. The result shows that the cumulative yield of GlcN and GlcNAc reaches 8.57 g/L, which is increased 2.4 times compared with the yield of single expression of gls (FIG. 7).

Figure 8:
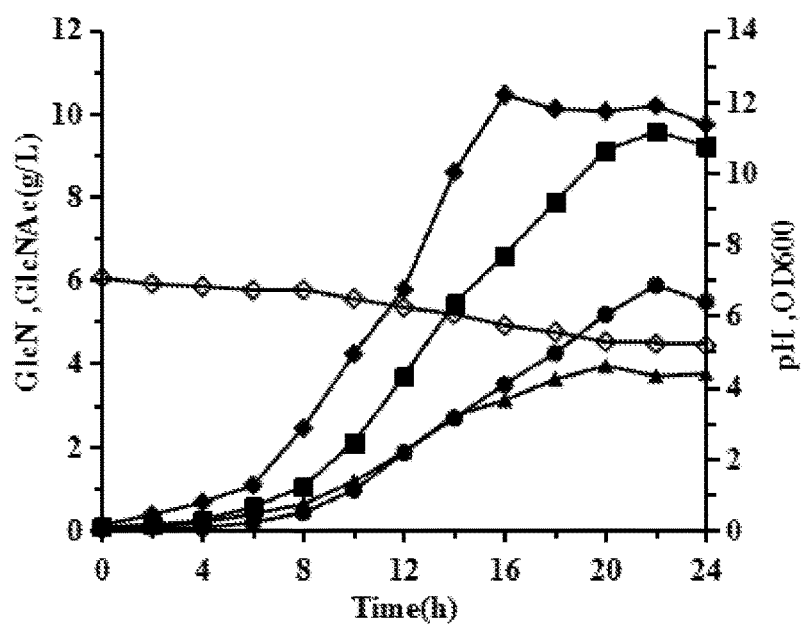
FIG. 8 is the yield of GlcN and GlcNAc in 7 L fermentation broth.
In the figure: •: GlcNAc, ▲: GlcN, ■: GlcNAc+GlcNAc, ♦: OD600, ◊: pH.

The fed-batch fermentation is conducted in 7 L numerical control fermenter. The fermentation is conducted with an initial loading volume of 4 L, an inoculation amount of 5% vol at 37° C. firstly, and change to 25° C. after induction. Due to the acid generated in the fermentation process, ammonia is added to adjust pH in the experiment. FIG. 8 is a fed-batch fermentation process curve of the 7 L fermenter. The biomass $OD_{600}$ reaches the maximum at 16 h, while the concentrations of GlcN, GlcNAc reach the maximum after 20 h, with the yield of 3.93 g/L, 5.86 g/L respectively. The cumulant of both reaches the maximum at 22 h, with the amount of 9.79 g/L.

The above disclosure shows some specific embodiments of the present invention, however, the present invention is not limited to these embodiments. Various modifications of the disclosed embodiments as well as alternative embodiments of the invention will become apparent to persons skilled in the art. It is therefore contemplated that the appended claims will cover any such modifications or embodiments that fall within the scope of the invention.

What is claimed is:

1. A directionally modified glucosamine synthase mutant, having the amino acid sequence of SEQ ID No: 1.

2. The directionally modified glucosamine synthase mutant according to claim 1, wherein a gene encoding the directionally modified glucosamine synthase mutant have the nucleotide sequence of SEQ ID No: 2.

3. A method for biosynthesizing a glucosamine by using a directionally modified glucosamine synthase mutant, comprising the following step: converting glucosamine of a fermentation system into acetylated glucosamine through co-expressing the directionally modified glucosamine synthase mutant and a glucosamine acetyltransferase; wherein the directionally modified glucosamine synthase mutant has the amino acid sequence of SEQ ID No: 1.

* * * * *

SEQUENCE LISTING

```
<160> NUMBER OF SEQ ID NOS: 8

<210> SEQ ID NO 1
<211> LENGTH: 600
<212> TYPE: PRT
<213> ORGANISM: Escherichia coli

<400> SEQUENCE: 1
```

-continued

```
Met Cys Gly Ile Val Gly Tyr Ile Gly Gln Leu Asp Ala Lys Glu Ile
1               5                   10                  15

Leu Leu Lys Gly Leu Glu Lys Leu Glu Tyr Arg Gly Tyr Asp Ser Ala
            20                  25                  30

Gly Ile Ala Val Ala Asn Glu Gln Gly Ile His Val Phe Lys Glu Lys
            35                  40                  45

Gly Arg Ile Ala Asp Leu Arg Glu Val Val Asp Ser Asn Val Glu Ala
        50                  55                  60

Lys Ala Gly Ile Gly His Thr Arg Trp Ala Thr His Gly Glu Pro Ser
65                  70                  75                  80

Tyr Leu Asn Ala His Pro His Gln Ser Ala Leu Gly Arg Phe Thr Leu
                85                  90                  95

Val His Asn Gly Val Ile Glu Asn Tyr Val Gln Leu Lys Gln Glu Tyr
            100                 105                 110

Leu Gln Asp Val Glu Leu Lys Ser Asp Thr Asp Thr Glu Val Val Ala
        115                 120                 125

Gln Val Ile Glu Gln Phe Val Asn Gly Gly Leu Glu Thr Glu Glu Ala
    130                 135                 140

Phe Arg Lys Thr Leu Thr Leu Leu Lys Gly Ser Tyr Ala Ile Ala Leu
145                 150                 155                 160

Phe Asp Asn Asp Asn Arg Glu Thr Ile Phe Val Ala Lys Asn Lys Ser
                165                 170                 175

Pro Leu Leu Val Gly Leu Gly Asp Thr Phe Asn Val Val Ala Ser Asp
            180                 185                 190

Ala Met Ala Met Leu Gln Val Thr Asn Glu Tyr Val Glu Leu Met Asp
        195                 200                 205

Lys Glu Met Val Ile Val Thr Asp Asp Gln Val Val Ile Lys Asn Leu
210                 215                 220

Asp Gly Asp Val Ile Thr Arg Ala Ser Tyr Ile Ala Glu Leu Asp Ala
225                 230                 235                 240

Ser Asp Ile Glu Lys Gly Thr Tyr Pro His Tyr Met Leu Lys Glu Thr
                245                 250                 255

Asp Glu Gln Pro Val Val Met Arg Lys Ile Ile Gln Thr Tyr Gln Asp
            260                 265                 270

Glu Asn Gly Lys Leu Ser Val Pro Gly Asp Ile Ala Ala Val Ala
        275                 280                 285

Glu Ala Asp Arg Ile Tyr Ile Ile Gly Cys Gly Thr Ser Tyr His Ala
    290                 295                 300

Gly Leu Val Gly Lys Gln Tyr Ile Glu Met Trp Ala Asn Val Pro Val
305                 310                 315                 320

Glu Val His Val Ala Ser Glu Phe Ser Tyr Asn Met Pro Leu Leu Ser
                325                 330                 335

Lys Lys Pro Leu Phe Ile Phe Leu Ser Gln Ser Gly Glu Thr Ala Ala
            340                 345                 350

Ser Cys Ala Val Leu Val Gln Val Lys Ala Leu Gly His Lys Ala Leu
        355                 360                 365

Thr Ile Thr Asn Val Pro Gly Ser Thr Leu Ser Arg Glu Ala Asp Tyr
    370                 375                 380

Thr Leu Leu Leu His Ala Gly Pro Glu Ile Ala Val Ala Ser Thr Lys
385                 390                 395                 400

Ala Tyr Thr Ala Gln Ile Ala Val Leu Ala Val Leu Ala Ser Val Ala
                405                 410                 415
```

```
Ala Asp Lys Asn Gly Met Asn Ile Gly Phe Asp Leu Val Lys Glu Val
            420                 425                 430

Gly Ile Ala Ala Asn Ala Met Glu Ala Leu Cys Asp Gln Lys Asp Glu
        435                 440                 445

Met Glu Met Ile Ala Arg Glu Tyr Leu Thr Val Ser Arg Asn Ala Phe
450                 455                 460

Phe Ile Gly Arg Gly Leu Glu Tyr Phe Val Cys Val Glu Gly Ala Leu
465                 470                 475                 480

Lys Leu Lys Glu Ile Ser Tyr Ile Gln Ala Glu Gly Phe Ala Gly Gly
                485                 490                 495

Glu Leu Lys His Gly Thr Ile Ala Leu Ile Glu Gln Gly Thr Pro Val
            500                 505                 510

Phe Ala Leu Ala Thr Gln Glu His Val Asn Leu Ser Ile Arg Gly Asn
        515                 520                 525

Val Lys Glu Val Ala Ala Arg Gly Ala Asn Thr Cys Ile Ile Ser Leu
530                 535                 540

Lys Gly Leu Asp Asp Ala Asp Asp Arg Phe Val Pro Pro Glu Val Asn
545                 550                 555                 560

Pro Ala Leu Ala Pro Leu Glu Ser Val Val Pro Leu Gln Leu Ile Ala
                565                 570                 575

Tyr Tyr Ala Ala Leu His Arg Gly Cys Asp Val Asp Lys Pro Arg Asn
            580                 585                 590

Leu Ala Lys Ser Val Thr Val Glu
            595                 600
```

<210> SEQ ID NO 2
<211> LENGTH: 1803
<212> TYPE: DNA
<213> ORGANISM: Escherichia coli

<400> SEQUENCE: 2

```
atgtgcggca ttgtgggtta tatcggccag ctggatgcaa agaaattct  gctgaaaggt      60
ctggaaaaac tggaatatcg cggttacgat agcgcgggca ttgctgtcgc gaacgaacaa     120
ggtatccatg tgttcaaaga aaaggccgt  attgccgatc tgcgcgaagt ggttgactca     180
aacgtggaag ccaaagcagg catcggtcat acccgttggg caacgcacgg cgaaccgagt     240
tacctgaatg ctcatccgca ccagtccgcg ctgggtcgtt ttaccctggt gcacaacggc     300
gttattgaaa attatgtgca gctgaaacaa gaatacctgc aagatgttga actgaaaagc     360
gataccgaca cggaagtcgt ggctcaggtt atcgaacaat ttgtcaatgg cggtctggaa     420
accgaagaag cgttccgcaa aaccctgacg ctgctgaaag gttcttatgc tattgcgctg     480
tttgataacg acaatcgtga acgatcttc  gtggccaaaa acaaatcacc gctgctggtt     540
ggcctgggtg ataccttcaa tgtcgtggca tcggacgcga tggcgatgct gcaggtgacg     600
aacgaatatg ttgaactgat ggataaagaa atggttattg tcaccgatga ccaagttgtc     660
atcaaaaatc tggatggtga cgtgattacg cgtgcaagct acatcgctga actggatgcg     720
tctgacattg aaaaaggcac ctatccgcat tacatgctga agaaacgga tgaacagccg     780
gtggttatgc gcaaaattat ccagacctat caagatgaaa acgtaaaact gagcgttccg     840
ggcgatattg cggcggcagt cgctgaagcg gaccgtatct atattatcgg ctgtggcacg     900
tcttaccatg cgggtctggt gggcaaacag tatattgaaa tgtgggccaa cgtgccggtt     960
gaagtccacg tggcaagtga attttcctac aatatgccgc tgctgagtaa aaaaccgctg    1020
tttatttttc ctgagccagtc tggcgaaacc gccgcttcct gcgcagttct ggtccaagtg    1080
```

```
aaagccctgg gtcataaagc actgaccatc acgaatgtgc cgggctcaac cctgtcgcgt    1140
gaagctgatt atacgctgct gctgcacgcg ggtccggaaa ttgccgttgc aagcaccaaa    1200
gcgtatacgg cacagatcgc agtcctggca gtgctggctt ctgtggctgc ggataaaaac    1260
ggtatgaata tcggctttga cctggttaaa gaagtgggca ttgccgcaaa cgcgatggaa    1320
gccctgtgcg atcagaaaga cgaaatggaa atgattgctc gtgaatatct gaccgtgagt    1380
cgcaatgcct ttttcatcgg ccgtggtctg gagtattttg tttgtgtcga aggtgccctg    1440
aaactgaaag aaatttccta catccaggct gaaggcttcg cgggcggtga actgaaacat    1500
ggtaccattg cgctgatcga acagggcacc ccggtctttg ctctggcgac gcaagaacac    1560
gttaacctgt caattcgcgg taatgttaaa gaagtcgctg cgcgtggcgc aaacacctgc    1620
attatctcgc tgaaaggtct ggatgacgcg atgaccgct tgtcccgcc ggaagtgaat    1680 ccggcactgg caccgctgga gagtgtcgtg ccgctgcagc tgatcgcgta ttacgccgca    1740
ctgcatcgcg gctgtgatgt tgacaaaccg cgtaacctgg ccaaaagcgt gaccgttgaa    1800
taa                                                                 1803
```

<210> SEQ ID NO 3
<211> LENGTH: 600
<212> TYPE: PRT
<213> ORGANISM: Escherichia coli

<400> SEQUENCE: 3

```
Met Cys Gly Ile Val Gly Tyr Ile Gly Gln Leu Asp Ala Lys Glu Ile
1               5                   10                  15

Leu Leu Lys Gly Leu Glu Lys Leu Glu Tyr Arg Gly Tyr Asp Ser Ala
            20                  25                  30

Gly Ile Ala Val Ala Asn Glu Gln Gly Ile His Val Phe Lys Glu Lys
        35                  40                  45

Gly Arg Ile Ala Asp Leu Arg Glu Val Asp Ala Asn Val Glu Ala
    50                  55                  60

Lys Ala Gly Ile Gly His Thr Arg Trp Ala Thr His Gly Glu Pro Ser
65                  70                  75                  80

Tyr Leu Asn Ala His Pro His Gln Ser Ala Leu Gly Arg Phe Thr Leu
                85                  90                  95

Val His Asn Gly Val Ile Glu Asn Tyr Val Gln Leu Lys Gln Glu Tyr
            100                 105                 110

Leu Gln Asp Val Glu Leu Lys Ser Asp Thr Asp Thr Glu Val Val Val
        115                 120                 125

Gln Val Ile Glu Gln Phe Val Asn Gly Gly Leu Glu Thr Glu Glu Ala
    130                 135                 140

Phe Arg Lys Thr Leu Thr Leu Leu Lys Gly Ser Tyr Ala Ile Ala Leu
145                 150                 155                 160

Phe Asp Asn Asp Asn Arg Glu Thr Ile Phe Val Ala Lys Asn Lys Ser
                165                 170                 175

Pro Leu Leu Val Gly Leu Gly Asp Thr Phe Asn Val Val Ala Ser Asp
            180                 185                 190

Ala Met Ala Met Leu Gln Val Thr Asn Glu Tyr Val Glu Leu Met Asp
        195                 200                 205

Lys Glu Met Val Ile Val Thr Asp Asp Gln Val Val Ile Lys Asn Leu
    210                 215                 220

Asp Gly Asp Val Ile Thr Arg Ala Ser Tyr Ile Ala Glu Leu Asp Ala
225                 230                 235                 240
```

Ser Asp Ile Glu Lys Gly Thr Tyr Pro His Tyr Met Leu Lys Glu Thr
            245                 250                 255

Asp Glu Gln Pro Val Val Met Arg Lys Ile Ile Gln Thr Tyr Gln Asp
        260                 265                 270

Glu Asn Gly Lys Leu Ser Val Pro Gly Asp Ile Ala Ala Val Ala
            275                 280                 285

Glu Ala Asp Arg Ile Tyr Ile Ile Gly Cys Gly Thr Ser Tyr His Ala
    290                 295                 300

Gly Leu Val Gly Lys Gln Tyr Ile Glu Met Trp Ala Asn Val Pro Val
305                 310                 315                 320

Glu Val His Val Ala Ser Glu Phe Ser Tyr Asn Met Pro Leu Leu Ser
            325                 330                 335

Lys Lys Pro Leu Phe Ile Phe Leu Ser Gln Ser Gly Glu Thr Ala Asp
            340                 345                 350

Ser Arg Ala Val Leu Val Gln Val Lys Ala Leu Gly His Lys Ala Leu
        355                 360                 365

Thr Ile Thr Asn Val Pro Gly Ser Thr Leu Ser Arg Glu Ala Asp Tyr
    370                 375                 380

Thr Leu Leu Leu His Ala Gly Pro Glu Ile Ala Val Ala Ser Thr Lys
385                 390                 395                 400

Ala Tyr Thr Ala Gln Ile Ala Val Leu Ala Val Leu Ala Ser Val Ala
            405                 410                 415

Ala Asp Lys Asn Gly Ile Asn Ile Gly Phe Asp Leu Val Lys Glu Leu
        420                 425                 430

Gly Ile Ala Ala Asn Ala Met Glu Ala Leu Cys Asp Gln Lys Asp Glu
    435                 440                 445

Met Glu Met Ile Ala Arg Glu Tyr Leu Thr Val Ser Arg Asn Ala Phe
450                 455                 460

Phe Ile Gly Arg Gly Leu Asp Tyr Phe Val Cys Val Glu Gly Ala Leu
465                 470                 475                 480

Lys Leu Lys Glu Ile Ser Tyr Ile Gln Ala Glu Gly Phe Ala Gly Gly
            485                 490                 495

Glu Leu Lys His Gly Thr Ile Ala Leu Ile Glu Gln Gly Thr Pro Val
        500                 505                 510

Phe Ala Leu Ala Thr Gln Glu His Val Asn Leu Ser Ile Arg Gly Asn
    515                 520                 525

Val Lys Glu Val Ala Ala Arg Gly Ala Asn Thr Cys Ile Ile Ser Leu
530                 535                 540

Lys Gly Leu Asp Asp Ala Asp Asp Arg Phe Val Leu Pro Glu Val Asn
545                 550                 555                 560

Pro Ala Leu Ala Pro Leu Val Ser Val Val Pro Leu Gln Leu Ile Ala
            565                 570                 575

Tyr Tyr Ala Ala Leu His Arg Gly Cys Asp Val Asp Lys Pro Arg Asn
        580                 585                 590

Leu Ala Lys Ser Val Thr Val Glu
        595                 600

<210> SEQ ID NO 4
<211> LENGTH: 1803
<212> TYPE: DNA
<213> ORGANISM: Escherichia coli

<400> SEQUENCE: 4
atgtgcggca ttgtgggtta tatcggccag ctggatgcaa agaaattct gctgaaaggt    60

-continued

```
ctggaaaaac tggaatatcg cggttacgat agcgcgggca ttgctgtcgc gaacgaacaa    120
ggtatccatg tgttcaaaga aaaggccgt attgccgatc tgcgcgaagt ggttgacgca     180
aacgtggaag ccaaagcagg catcggtcat acccgttggg caacgcacgg cgaaccgagt    240
tacctgaatg ctcatccgca ccagtccgcg ctgggtcgtt ttaccctggt gcacaacggc    300
gttattgaaa attatgtgca gctgaaacaa gaatacctgc aagatgttga actgaaaagc    360
gataccgaca cggaagtcgt ggttcaggtt atcgaacaat tgtcaatgg cggtctggaa     420 accgaagaag cgttccgcaa acccctgacg ctgctgaaag gttcttatgc tattgcgctg    480
tttgataacg acaatcgtga aacgatcttc gtggccaaaa acaaatcacc gctgctggtt    540
ggcctgggtg ataccttcaa tgtcgtggca tcggacgcga tggcgatgct gcaggtgacg    600
aacgaatatg ttgaactgat ggataaagaa atggttattg tcaccgatga ccaagttgtc    660
atcaaaaatc tggatggtga cgtgattacg cgtgcaagct acatcgctga actggatgcg    720
tctgacattg aaaaaggcac ctatccgcat tacatgctga agaaacgga tgaacagccg     780 gtggttatgc gcaaaattat ccagacctat caagatgaaa acggtaaact gagcgttccg    840
ggcgatattg cggcggcagt cgctgaagcg accgtatct atattatcgg ctgtggcacg     900
tcttaccatg cgggtctggt gggcaaacag tatattgaaa tgtgggccaa cgtgccggtt    960
gaagtccacg tggcaagtga attttcctac aatatgccgc tgctgagtaa aaaaccgctg    1020
tttattttcc tgagccagtc tggcgaaacc gccgattccc gcgcagttct ggtccaagtg    1080
aaagccctgg gtcataaagc actgaccatc acgaatgtgc cgggctcaac cctgtcgcgt    1140
gaagctgatt atacgctgct gctgcacgcg ggtccggaaa ttgccgttgc aagcaccaaa    1200
gcgtatacgg cacagatcgc agtcctggca gtgctggctt ctgtggctgc ggataaaaac    1260
ggtattaata tcggctttga cctggttaaa gaactgggca ttgccgcaaa cgcgatggaa    1320
gccctgtgcg atcagaaaga cgaaatgaaa atgattgctc gtgaatatct gaccgtgagt    1380
cgcaatgcct ttttcatcgg ccgtggtctg gattattttg tttgtgtcga aggtgccctg    1440
aaactgaaag aaatttccta catccaggct gaaggcttcg cgggcggtga actgaaacat    1500
ggtaccattg cgctgatcga acagggcacc ccggtctttg ctctggcgac gcaagaacac    1560
gttaacctgt caattcgcgg taatgttaaa gaagtcgctg cgcgtggcgc aaacacctgc    1620
attatctcgc tgaaaggtct ggatgacgcg gatgaccgct tgtcctgcc ggaagtgaat     1680 ccggcactgg caccgctggt gagtgtcgtg ccgctgcagc tgatcgcgta ttacgccgca    1740
ctgcatcgcg gctgtgatgt tgacaaaccg cgtaacctgg ccaaaagcgt gaccgttgaa    1800
taa                                                                 1803
```

<210> SEQ ID NO 5
<211> LENGTH: 30
<212> TYPE: DNA
<213> ORGANISM: Artificial Sequence
<220> FEATURE:
<223> OTHER INFORMATION: The sequence is synthesized

<400> SEQUENCE: 5

```
cgcggatcca tgtgtggaat cgtaggttat                                     30
```

<210> SEQ ID NO 6
<211> LENGTH: 33
<212> TYPE: DNA
<213> ORGANISM: Artificial Sequence
<220> FEATURE:

```
<223> OTHER INFORMATION: The sequence is synthesized

<400> SEQUENCE: 6
ccggaattct tattcaacgg tcacgctttt ggc                          33

<210> SEQ ID NO 7
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 7
cccaagctta aggagatata ccatgagcct gccggatggt ttt               43

<210> SEQ ID NO 8
<211> LENGTH: 33
<212> TYPE: DNA
<213> ORGANISM: Artificial Sequence
<220> FEATURE:
<223> OTHER INFORMATION: The sequence is synthesized

<400> SEQUENCE: 8
ccgctcgagt tatttacgaa tttgcatttc gac                          33
```